US012367950B2

(12) United States Patent
Murase et al.

(10) Patent No.: US 12,367,950 B2
(45) Date of Patent: Jul. 22, 2025

(54) GLYCAN STRUCTURE ANALYZER AND GLYCAN STRUCTURE ANALYSIS PROGRAM

(71) Applicant: SHIMADZU CORPORATION, Kyoto (JP)

(72) Inventors: Masaki Murase, Kyoto (JP); Takashi Nishikaze, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 801 days.

(21) Appl. No.: 17/283,798

(22) PCT Filed: May 23, 2019

(86) PCT No.: PCT/JP2019/020413
§ 371 (c)(1),
(2) Date: Apr. 8, 2021

(87) PCT Pub. No.: WO2020/079878
PCT Pub. Date: Apr. 23, 2020

(65) Prior Publication Data
US 2021/0391035 A1   Dec. 16, 2021

(30) Foreign Application Priority Data
Oct. 16, 2018   (JP) .................. 2018-195196

(51) Int. Cl.
*G16C 20/20*   (2019.01)
*G16B 40/10*   (2019.01)
*H01J 49/00*   (2006.01)

(52) U.S. Cl.
CPC ............ *G16C 20/20* (2019.02); *G16B 40/10* (2019.02); *H01J 49/0036* (2013.01)

(58) Field of Classification Search
CPC ..... G16C 20/20; G16B 40/10; H01J 49/0036; H01J 49/26
(Continued)

(56) References Cited

U.S. PATENT DOCUMENTS

2018/0059094 A1   3/2018   Nishikaze
2019/0120793 A1*  4/2019   Nishikaze .............. G01N 27/62
(Continued)

FOREIGN PATENT DOCUMENTS

| EP | 3 457 123 A1 | 3/2019 |
| JP | 2016-194500 A | 11/2016 |
| JP | 6135710 B2 | 5/2017 |
| WO | WO-2017145496 A1 * | 8/2017 ............. G01N 27/62 |

OTHER PUBLICATIONS

English translation of WO 2017145496, Aug. 31, 2017. (Year: 2017).*
(Continued)

*Primary Examiner* — Michael P Nghiem
(74) *Attorney, Agent, or Firm* — Sughrue Mion, PLLC (57) ABSTRACT

In a glycan structure analyzer according to one mode, a plurality of tabs for setting analysis conditions includes a dedicated tab for the setting of the conditions concerning a chemical modification specific to the linkage type of sialic acids, allowing a user to select major chemical modification agents. When one of those agents is selected, the mass change for each linkage type is automatically set. When using a chemical modification other than the preset ones, the user can input a numerical value of the amount of mass change for each linkage type. In an analysis, theoretical m/z values of a plurality of glycan structure candidates having different m/z values depending on the linkage type corresponding to one chemical modification are simultaneously compared with the m/z values of measured ion peaks.

11 Claims, 5 Drawing Sheets

(58) Field of Classification Search
USPC .......................................................... 702/27
See application file for complete search history.

(56) References Cited

U.S. PATENT DOCUMENTS

| | | | |
|---|---|---|---|
| 2020/0109159 A1* | 4/2020 | Nishikaze | G01N 33/6848 |
| 2021/0104299 A1* | 4/2021 | Baba | H01J 49/0068 |
| 2022/0189756 A1* | 6/2022 | Murase | H01J 49/40 |

OTHER PUBLICATIONS

Takashi Nishikaze et al., "Differentiation of Sialyl Linkage Isomers by One-Pot Sialic Acid Derivatization for Mass Spectrometry-Based Glycan Profiling", Analytical Chemistry, 2017, pp. 2353-2360, vol. 89.
Kai Maass et al., ""Glyco-peakfinder"—denovo composition anlysis of glycoconjugates", Proteomics, 2007, pp. 4435-4444, vol. 7, No. 24.
Arun Apte et al., "Bioinformatics in Glycomics: Glycan Characterization with Mass Spectrometric Data Using SimGlycan", Bioinformatics in Glycomics, Functional Glycomic, Methods in Molecular Biology, Humana Press, 2010, pp. 269-281.
International Search Report for PCT/JP2019/020413 dated Aug. 27, 2019 [PCT/ISA/210].
Written Opinion for PCT/JP2019/020413 dated Aug. 27, 2019 [PCT/ISA/237].
Extended European Search Report dated Nov. 12, 2021 from the European Patent Office in European Application No. 19872899.0.
Chinese Office Action issued Jan. 22, 2024 in Application No. 201980066629.7.

* cited by examiner

| Detected m/z | No. | Candidates for glycan composition | Mass (Theoretical) | Deviation [ppm] |
|---|---|---|---|---|
| 2,471.88 | 1 | Hex5HexNAc4Neu5Ac(a2,3)2-3AQ | 2,471.88 | -6.8 |
|  | 2 | dHex3Hex4HexNAc4Neu5Ac(a2,6)1-3AQ | 2,471.89 | 3.2 |
| 2,499.92 | 1 | Hex5HexNAc4Neu5Ac(a2,3)1Neu5Ac(a2,6)1-3AQ | 2,499.89 | -10.3 |
|  | 2 | dHex2Hex4HexNAc2Neu5Ac(a2,3)3-3AQ | 2,499.89 | -10.2 |
| 2,527.94 | 1 | S1dHex4Hex5HexNAc4-3AQ | 2,527.80 | -56.4 |
|  | 2 | dHex4Hex8HexNAc2-3AQ | 2,527.84 | -39.5 |
|  | 3 | Hex5HexNAc4Neu5Ac(a2,6)2-3AQ | 2,527.93 | -5.8 |
|  | 4 | dHex2Hex4HexNAc2Neu5Ac(a2,3)2Neu5Ac(a2,6)1-3AQ | 2,527.93 | -5.7 |
| 2,865.06 | 1 | S1Hex3HexNAc7Neu5Ac(a2,3)1Neu5Ac(a2,6)1-3AQ | 2,864.98 | -25.7 |
|  | 2 | Hex6HexNAc5Neu5Ac(a2,3)1Neu5Ac(a2,6)1-3AQ | 2,865.03 | -11.8 |
|  | 3 | dHex2Hex5HexNAc3Neu5Ac(a2,3)3-3AQ | 2,865.03 | -11.7 |
| 3,141.10 | 1 | S2Hex7HexNAc3Neu5Ac(a2,6)3-3AQ | 3,141.02 | -24.5 |
|  | 2 | S1Hex3HexNAc7Neu5Ac(a2,3)3-3AQ | 3,141.08 | -6.6 |
|  | 3 | Hex6HexNAc5Neu5Ac(a2,3)3-3AQ | 3,141.12 | 7.1 |
|  | 4 | dHex3Hex5HexNAc5Neu5Ac(a2,3)1Neu5Ac(a2,6)1-3AQ | 3,141.15 | 15 |
| 3,169.18 | 1 | S2dHex2Hex4HexNAc9-3AQ | 3,168.98 | -62.4 |
|  | 2 | S1dHex2Hex7HexNAc7-3AQ | 3,169.02 | -48.9 |
|  | 3 | dHex2Hex10HexNAc5-3AQ | 3,169.07 | -35.4 |
|  | 4 | S1Hex3HexNAc7Neu5Ac(a2,3)2Neu5Ac(a2,6)1-3AQ | 3,169.11 | -21.9 |
|  | 5 | Hex6HexNAc5Neu5Ac(a2,3)2Neu5Ac(a2,6)1-3AQ | 3,169.15 | -8.4 |
|  | 6 | dHex2Hex5HexNAc3Neu5Ac(a2,3)4-3AQ | 3,169.15 | -8.3 |
|  | 7 | dHex3Hex5HexNAc5Neu5Ac(a2,6)2-3AQ | 3,169.18 | -0.6 |
| 3,197.26 | 1 | S2dHex4Hex3HexNAc7Neu5Ac(a2,3)1-3AQ | 3,197.01 | -77.1 |
|  | 2 | S1dHex4Hex6HexNAc5Neu5Ac(a2,3)1-3AQ | 3,197.06 | -63.7 |
|  | 3 | dHex4Hex9HexNAc3Neu5Ac(a2,3)1-3AQ | 3,197.10 | -50.3 |
|  | 4 | S1Hex3HexNAc7Neu5Ac(a2,3)1Neu5Ac(a2,6)2-3AQ | 3,197.14 | -37.1 |
|  | 5 | Hex6HexNAc5Neu5Ac(a2,3)1Neu5Ac(a2,6)2-3AQ | 3,197.18 | -23.7 |
|  | 6 | dHex2Hex5HexNAc3Neu5Ac(a2,3)3Neu5Ac(a2,6)1-3AQ | 3,197.18 | -23.6 |
| 3,501.38 | 1 | S2dHex2Hex4HexNAc9Neu5Ac(a2,6)1-3AQ | 3,501.14 | -71.4 |
|  | 2 | S2dHex4Hex3HexNAc7Neu5Ac(a2,3)2-3AQ | 3,501.14 | -71.3 |
|  | 3 | S1dHex2Hex7HexNAc7Neu5Ac(a2,6)1-3AQ | 3,501.18 | -59.1 |
|  | 4 | S1dHex4Hex6HexNAc5Neu5Ac(a2,3)2-3AQ | 3,501.18 | -59 |
|  | 5 | dHex2Hex10HexNAc5Neu5Ac(a2,6)1-3AQ | 3,501.23 | -46.9 |
|  | 6 | dHex4Hex9HexNAc3Neu5Ac(a2,3)2-3AQ | 3,501.23 | -46.8 |
|  | 7 | S1Hex3HexNAc7Neu5Ac(a2,3)2Neu5Ac(a2,6)2-3AQ | 3,501.27 | -34.7 |
|  | 8 | Hex6HexNAc5Neu5Ac(a2,3)2Neu5Ac(a2,6)2-3AQ | 3,501.31 | -22.5 |
|  | 9 | dHex2Hex5HexNAc3Neu5Ac(a2,3)4Neu5Ac(a2,6)1-3AQ | 3,501.31 | -22.4 |
|  | 10 | dHex3Hex5HexNAc5Neu5Ac(a2,6)3-3AQ | 3,501.34 | -15.4 |
| 3,529.40 | 1 | S2dHex1Hex4HexNAc7Neu5Ac(a2,3)3-3AQ | 3,529.15 | -71.7 |
|  | 2 | S2dHex4Hex3HexNAc7Neu5Ac(a2,3)1Neu5Ac(a2,6)1-3AQ | 3,529.17 | -64.7 |
|  | 3 | S1dHex1Hex7HexNAc5Neu5Ac(a2,3)3-3AQ | 3,529.19 | -59.6 |
|  | 4 | S1dHex4Hex6HexNAc5Neu5Ac(a2,3)1Neu5Ac(a2,6)1-3AQ | 3,529.21 | -52.6 |
|  | 5 | dHex1Hex10HexNAc3Neu5Ac(a2,3)3-3AQ | 3,529.23 | -47.5 |
|  | 6 | dHex4Hex9HexNAc3Neu5Ac(a2,3)1Neu5Ac(a2,6)1-3AQ | 3,529.26 | -40.5 |
|  | 7 | Hex4HexNAc13-3AQ | 3,529.27 | -36.8 |
|  | 8 | S1Hex3HexNAc7Neu5Ac(a2,3)1Neu5Ac(a2,6)3-3AQ | 3,529.30 | -28.5 |
|  | 9 | Hex6HexNAc5Neu5Ac(a2,3)1Neu5Ac(a2,6)3-3AQ | 3,529.34 | -16.4 |
|  | 10 | dHex2Hex5HexNAc3Neu5Ac(a2,3)3Neu5Ac(a2,6)2-3AQ | 3,529.34 | -16.3 |

Fig. 5

| PEAK m/z |
|---|
| 2471.880000 |
| 2499.920000 |
| 2527.940000 |
| 2865.060000 |
| 3141.100000 |
| 3169.180000 |
| 3197.260000 |
| 3501.390000 |
| 3529.400000 |

Fig. 6

| SETTINGS | | MASS SHIFT |
|---|---|---|
| LABEL MODIFICATION | | |
| | On-target 3AQ labelling | 126.0582 |
| ION SPECIES | | |
| | Charge | 1 |
| | HSO4-added Ion | 96.9596 |
| SALT FORMATION | | |
| | Maximum Substitutions | 0 |
| SIALIC-ACID-LINKAGE-SPECIFIC CHEMICAL MODIFICATION | | 41.0629/ 13.0316 |
| | Isopropylamide/Methylamide | |

Fig. 7

| SETTINGS | | MASS OF RESIDUE | MINIMUM NUMBER | MAXIMUM NUMBER |
|---|---|---|---|---|
| MONOSACCHARIDES | | | | |
| | Hexose | 162.0528 | 3 | 15 |
| | N-Acetyl Hexosamine | 203.0794 | 2 | 14 |
| | Fucose (deoxyhexose) | 146.0579 | 0 | 4 |
| MODIFICATION | | | | |
| | Sulfate | 70.0568 | 0 | 2 |
| SIALIC ACID | | | | |
| | N-Acetyl neuraminic acid | 291.0954 | 0 | 5 |

— # GLYCAN STRUCTURE ANALYZER AND GLYCAN STRUCTURE ANALYSIS PROGRAM

CROSS REFERENCE TO RELATED APPLICATIONS

This application is a National Stage of International Application No. PCT/JP2019/020413 filed May 23, 2019, claiming priority based on Japanese Patent Application No. 2018-195196 filed Oct. 16, 2018.

TECHNICAL FIELD

The present invention relates to a glycan structure analyzer configured to analyze the structure of a glycan by using mass spectrometry, as well as a glycan structure analysis program for analyzing the structure of a glycan on a computer. More specifically, it relates to a glycan structure analyzer and glycan structure analysis program capable of analyzing the glycan structure including the glycosidic linkage type of a sialic acid. The term "glycan" in the present description includes not only a glycan in its independent form but also a form of a glycosylation, i.e., a glycan modifying a protein, peptide, lipid, nucleic acid or other kinds of biomolecules.

BACKGROUND ART

The process of the biosynthesis of proteins, peptides or other biomolecules in living organisms is finely controlled. Therefore, it has been considered that glycosylated biomolecules produced in the biosynthetic process should play important roles in vital activities. In recent years, a considerable number of concrete reports at the level of glycan molecules have been made, particularly on the relationship of those molecules with physiology or diseases. With such a background, it has been expected that revealing the structures of glycans modifying biomolecules involved in various processes in vital phenomena will be useful for the elucidation of vital phenomena as well as the drug discovery and diagnosis.

Sialic acids, which are a kind of sugar, has been considered to be an important type of substance for the quality control of proteins, signal transduction in the nervous system, mutual recognition of cells or other aspects of vital actions. In recent years, it has been gradually revealed that the form in which a sialic acid residue is linked to the terminal of a glycan, i.e., the difference in the linkage type of the sialic acid residue, is important for those organic activities. Therefore, recognizing the linkage type of a sialic acid to a glycan is an important task in the glycan structure analysis.

For example, in the case of human beings, α2,3 and α2,6 linkages have been known as the main linkage types of sialic acids. It has been known the linkage type changes with the cancerization of a cell. Accordingly, it is expected that the linkage type can be used as a biomarker, for the quality control of biopharmaceuticals, or for other purposes. However, glycan isomers which only differ from each other in the linkage types of the included sialic acids have no difference in mass. Therefore, it is difficult to determine their linkage types by mass spectrometers, which are widely used for glycan analyses. Another problem is the low level of detection sensitivity and quantitative accuracy, which is due to the fact that sialic acids are easy to be dissociated from the glycan and are unstable. Accordingly, the development of a technique capable of promptly and accurately analyzing the linkage types of sialic acids has been strongly desired.

With such a technical background, techniques for a chemical modification specific to the linkage types of sialic acids have been developed in order to stabilize the structure of the sialic acids and allow different linkage types to be distinguished by a mass spectrometer having a high level of throughput. For example, Patent Literature 1 and Non Patent Literature 1 disclose a technique in which the target sample including a glycan is made to react with a dehydration-condensation agent containing an amine (e.g., isopropyl amine) and a carbodiimide to produce a lactone as a glycan modifier with α2,3-linked sialic acids as well as an amide as a glycan modifier with α2,6-linked sialic acids. Those documents also disclose other methods for chemical modification.

In order to analyze the composition and structure of a glycan treated with the previously described chemical modification technique specific to the linkage type of sialic acids, it is necessary to perform a mass spectrometric analysis using a matrix-assisted laser desorption/ionization (MALDI) time-of-flight mass spectrometer (TOFMS) or the like, and analyze the thereby collected data with a computer. There are several conventionally known computer software applications for determining the glycan composition and structure from data acquired for a glycan by a mass spectrometric analysis. Representative examples include "Glyco-peak-finder" (see Non Patent Literature 2) and "SimGlycan®" (see Non Patent Literature 3).

Glyco-peakfinder tests all possible combinations of various monosaccharides to find a glycan composition whose mass coincides with the mass-to-charge-ratio value of a peak on a measured mass spectrum (this peak is hereinafter called the "ion peak") within a predetermined allowable error. SimGlycan determines the composition and structure of a glycan corresponding to the mass-to-charge ratios of the peaks on a measured MS/MS spectrum by a database search using a database originally constructed by the software manufacturer.

Those exiting software applications for glycan analysis can also be used for an analysis of glycan derivatives including glycan modifiers. However, in those applications, it is not assumed to perform an analysis of a glycan modifier formed by a chemical modification technique specific to the linkage type of sialic acids. Therefore, for example, in the case of performing an all-possibility search, a plurality of different modifiers which are obtained according to the difference in the linkage type of sialic acids through the user of one chemical modification agent specific to the linkage type of sialic acids must be individually searched for as a plurality of kinds of monosaccharide residues having different masses. If there are two possible linkage types for each of the N kinds of sialic acids, the user needs to determine 2×N sialic-acid modifiers and input them as additional monosaccharide residues to be searched. The aforementioned software applications normally have an upper limit of the number of monosaccharide residues that can be originally added as search targets by the user. This poses the problem that it is not always possible to search all combinations of the necessary kinds of sialic acids. In order to increase the number of search targets in such a case, the search needs to be performed a plurality of times under different search conditions, which consumes a considerable amount of labor and time. Furthermore, the task of additionally inputting and setting modifications is not only cumbersome but is also likely to incur a setting error.

CITATION LIST

Patent Literature

Patent Literature 1: JP 2016-194500 A

Non Patent Literature

Non Patent Literature 1: Takashi Nishikaze and five other authors, "Differentiation of Sialyl Linkage Isomers by One-Pot Sialic Acid Derivatization for Mass Spectrometry-Based Glycan Profiling", *Analytical Chemistry*, 2017, Vol. 89, pp. 2353-2360

Non Patent Literature 2: K. Maass and four other authors, "'Glyco-peakfinder'—De novo composition analysis of glycoconjugates", *Proteomics*, 2007, Vol. 7, No. 24, pp. 4435-4444

Non Patent Literature 3: A. Apte and another author, "Bioinformatics in Glycomics: Glycan Characterization with Mass Spectrometric Data Using SimGlycan", *Functional Glycomic, Methods in Molecular Biology*, Humana Press, 2010, pp. 269-281

SUMMARY OF INVENTION

Technical Problem

The present invention has been developed to solve the previously described problem. Its primary objective is to provide a glycan structure analyzer and a computer program for glycan structure analysis which can reduce the amount of labor for the setting of search conditions or other cumbersome tasks by the user, as well as efficiently perform the analysis, when analyzing a glycan structure including the linkage type of sialic acids based on mass spectrum data for a sample containing a glycan which has undergone a chemical modification specific to the linkage type of sialic acids.

Solution to Problem

A glycan structure analyzer according to the first mode of the present invention developed for solving the previously described problem is a glycan structure analyzer configured to analyze the structure of a sialic-acid-linked glycan based on mass spectrum data obtained by a mass spectrometric analysis of a sample containing the sialic-acid-linked glycan pretreated with a chemical modification agent specific to the sialic-acid linkage type or a molecule modified with the sialic-acid-linked glycan, the glycan structure analyzer including:
  a condition setting section configured to allow a user to set an ion species to be analyzed, the polarity of the electric charge of the ion species, and mass change factors each of which causes a mass change of a glycan through a modification;
  a glycan core structure information acquisition section configured to acquire various glycans having a core structure formed by a plurality of monosaccharide residues of a plurality of kinds, and mass information corresponding to each of those glycans;
  a theoretical mass calculation section configured to calculate a theoretical glycan mass-to-charge ratio for each of the various glycans acquired by the glycan core structure information acquisition section, by increasing or decreasing the mass of the glycan based on the mass change factors set through the condition setting section; and
  a glycan structure estimation section configured to estimate the structure of a glycan by comparing the theoretical glycan mass-to-charge ratio of the glycan with the mass-to-charge ratio of an ion peak in given mass spectrum data,
where:
  the condition setting section includes a mass change setting section for sialic-acid-linkage-specific chemical modification, configured to allow the user to set, as one of the mass change factors, a chemical modification specific to the linkage type of a sialic acid separately from other kinds of modifications; and
  the theoretical mass calculation section is configured to determine the theoretical glycan mass-to-charge ratio by increasing or decreasing the mass for each sialic-acid linkage type according to the chemical modification set through the mass change setting section for sialic-acid-linkage-specific chemical modification.

A glycan structure analysis program according to the first mode of the present invention developed for solving the previously described problem is a computer program for realizing the functions in the glycan structure analyzer according to the first mode of the present invention. Specifically, it is a glycan structure analysis program for analyzing the structure of a sialic-acid-linked glycan based on mass spectrum data obtained by a mass spectrometric analysis of a sample containing the sialic-acid-linked glycan pretreated with a chemical modification agent specific to the sialic-acid linkage type or a molecule modified with the sialic-acid-linked glycan, the program configured to make a computer function as:
  a condition setting functional section configured to allow a user to set an ion species to be analyzed, the polarity of the electric charge of the ion species, and mass change factors each of which causes a mass change of a glycan through a modification;
  a glycan core structure information acquisition functional section configured to acquire various glycans having a core structure formed by a plurality of monosaccharide residues of a plurality of kinds, and mass information corresponding to each of those glycans;
  a theoretical mass calculation functional section configured to calculate a theoretical glycan mass-to-charge ratio for each of the various glycans acquired by the glycan core structure information acquisition functional section, by increasing or decreasing the mass of the glycan based on the mass change factors set through the condition setting functional section; and
  a glycan structure estimation functional section configured to estimate the structure of a glycan by comparing the theoretical glycan mass-to-charge ratio of the glycan with the mass-to-charge ratio of an ion peak in given mass spectrum data,
where:
  the condition setting functional section is configured to allow the user to set, as one of the mass change factors, a sialic-acid-linkage-specific chemical modification which is a chemical modification specific to the linkage type of a sialic acid, separately from other kinds of modifications; and
  the theoretical mass calculation functional section is configured to calculate a theoretical glycan mass-to-charge ratio by increasing or decreasing the mass for each sialic-acid linkage type according to the set sialic-acid-linkage-specific chemical modification.

The glycan structure analysis program according to the first mode of the present invention is a program for operating an appropriate type of computer, such as a general-purpose personal computer, more sophisticated computer, or dedicated computer embedded in various kinds of systems. This type of program can be offered to users in the form of a non-transitory storage medium recording the program, such as a CD-ROM, DVD-ROM, memory card, or USB memory (dongle). It may also be offered to users in the form of data transferred through the Internet or similar communication networks. Understandably, in the case where a user newly purchases a system, the glycan structure analysis program according to the previously described mode can be previously installed on a computer included in that system.

In the present invention, an example of the "molecule modified with the sialic-acid-linked glycan" is a biomolecule, such as a protein, peptide, lipid or nucleic acid, modified with a glycan to which a sialic acid is linked. Examples of the pretreatment using a chemical modification agent specific to the sialic-acid linkage type (this treatment is a prerequisite for the present invention) include, but are not limited to, the pretreatments disclosed in Patent Literature 1 or Non Patent Literature 1. Any treatment may be used as long as it produces a specific chemical modification for distinguishing between two or more different linkage types of sialic acids, such as an α2,3-linked, α2,6-linked or α2,8-linked type.

The type of mass spectrometer and method of mass spectrometry for performing a mass spectrometric analysis of a sample containing a sialic-acid-linked glycan (or the like) are not specifically limited. For example, an ion trap mass spectrometer, linear ion trap mass spectrometer, TOF/TOF mass spectrometer, quadrupole time-of-flight (Q-TOF) mass spectrometer, quadrupole ion-trap mass spectrometer or Fourier-transform ion cyclotron resonance mass spectrometer can be used.

In the glycan structure analyzer according to the first mode of the present invention, for example, the condition setting section displays a predetermined condition-setting window on a screen of a display unit, and receives items of information entered or selected on the same window. This window is configured to allow the user to set, as search conditions for the glycan structure analysis, an ion species to be analyzed, the polarity of the electric charge of the ion species, and mass change factors. In particular, the user can set, as one of the mass change factors, a chemical modification specific to the linkage type of a sialic acid separately from other modifications. In other words, the user can set information concerning a chemical modification specific to the linkage type separately from information concerning other kinds of glycan modifications, such as the modification of a reducing terminal of a glycan which is often performed for the fluorescent labelling (or other purposes).

Specifically, for example, an independent window or tab on which the user can set the mass change factor due to the chemical modification specific to the linkage type may be provided separately from the main setting screen. As another example, a plurality of display areas may be arranged within one window, and one of those areas may be configured to allow the setting of the mass change factor due to the chemical modification specific to the linkage type.

When an analysis is initiated, the glycan core structure information acquisition section acquires various glycans having a core structure formed by a plurality of monosaccharide residues, and mass information corresponding to each of those glycans. There are specifically two possible methods for obtaining information concerning glycans having a core structure. One method is to find all possible glycans that can theoretically be formed. The other method is to perform a database search using an existing glycan structure database.

Thus, as one embodiment of the glycan structure analyzer according to the present invention, the glycan core structure information acquisition section may be configured to estimate all possible glycan structures under specific limiting conditions concerning the kinds and numbers of monosaccharide residues, and to determine various glycans having a core structure and mass information corresponding to each of those glycans.

As another embodiment, the glycan structure analyzer may further include a glycan structure database recording various glycan structures and masses, and the glycan core structure information acquisition section may be configured to determine various glycans having a core structure, by searching the information recorded in the glycan structure database, based on the mass information of the glycan set by the user.

The glycans obtained by the glycan core structure information acquisition section are in their respective original forms with no alteration, such as the modification, substitution, or addition of a specific substance in the ionization process. By comparison, the theoretical mass calculation functional section calculates the theoretical mass-to-charge ratio of each glycan in the form of an ion to be detected by mass spectrometry, by increasing or decreasing the mass of the glycan based on the mass change factors set through the condition setting section. If a chemical modification has been set through the mass change setting section for sialic-acid-linkage-specific chemical modification, the theoretical mass calculation functional section calculates a theoretical mass-to-charge ratio by increasing or decreasing the mass by a different amount for each sialic-acid linkage type according to the chemical modification. For example, in the case of a chemical modification which enables distinction between the α2,3-linked and α2,6-linked types, the mass of the glycan is increased by a different amount for each of the two linkage types. If there are N sialic acids contained in one kind of core glycan structure, a total of N+1 ($=_{N+2}C_N$) different theoretical glycan mass-to-charge ratios will be obtained.

The glycan structure estimation functional section compares the calculated theoretical glycan mass-to-charge ratios with the mass-to-charge ratios of ion peaks in given mass spectrum data. For each ion peak, theoretical mass-to-charge ratios whose deviations from the mass-to-charge ratio of the ion peak fall within a predetermined allowable range are selected as candidates for the glycan corresponding to the ion peak concerned. As noted earlier, for glycans having the same core structure, the mass-to-charge ratios of two or more modified glycan ions whose theoretical glycan mass-to-charge ratios are different from each other due to their difference in sialic-acid linkage type are obtained. Therefore, the correspondence between the ion peak and the two or more glycan ions can be simultaneously determined.

It is preferable for the glycan structure analyzer according to the present invention to further include a display processing section configured to display, on a display section, information concerning a glycan structure estimated by the glycan structure estimation section, where the display processing section is configured to display additional information showing the linkage type of each sialic acid if the estimated glycan structure includes sialic acids whose linkage types are identifiable.

Specifically, in the case of a chemical modification which enables distinction between the α2,3-linked and α2,6-linked types, character strings, marks or other types of information representing "α2,3-" and "α2,6-" can be added to the glycan compositions on the display. This allows the user to quickly recognize differences in linkage type of the sialic acids.

In the glycan structure analyzer according to the present invention, the mass change setting section for sialic-acid-linkage-specific chemical modification may be configured to allow the selection of a preset sialic-acid-linkage-specific chemical modification, as well as an input of a mass change value for each sialic-acid linkage type for other sialic-acid-linkage-specific chemical modifications.

According to this configuration, in the case of using a preset sialic-acid-linkage-specific chemical modification which is commonly and frequently used, the user only needs to perform a simple selecting operation to select the sialic-acid-linkage-specific chemical modification. In the case of using a sialic-acid-linkage-specific chemical modification which is rather uncommon or has not conventionally been used, the user can perform the estimation of the glycan structure corresponding to that chemical modification by directly inputting the mass change value for each sialic-acid linkage type.

Advantageous Effects of Invention

According to the present invention, in a glycan structure analysis using a chemical modification specific to the linkage type of sialic acids, the structures of a plurality of glycans (glycan modifiers) having different mass-to-charge ratios according to the difference in linkage type of the sialic acids included in one kind of glycan can be exhaustively searched with the setting of one sialic-acid-linkage-specific chemical modification and one analytical process. This reduces the amount of labor for the setting of the search conditions or other cumbersome tasks by the user in a glycan structure analysis including the linkage type of sialic acids. The time required for the analytical process can also be shortened, and the throughput of the analysis can be improved.

Furthermore, according to the present invention, in the case of using a chemical modification agent specific to the linkage type of a major sialic acid, the user only needs to select the desired one from a plurality of options prepared beforehand. It is unnecessary for the user to obtain the amount of mass change or other items of information, and manually input the information. This reduces the time and labor of the work as well as prevents incorrect operations due to the manual input.

BRIEF DESCRIPTION OF DRAWINGS

FIG. 4 shows a display example of the glycan structure estimation result in the glycan structure analyzing system according to the present embodiment.

DESCRIPTION OF EMBODIMENTS

A glycan structure analyzing system as one embodiment of the present invention is initially described with reference to the attached drawings.

Figure 1:
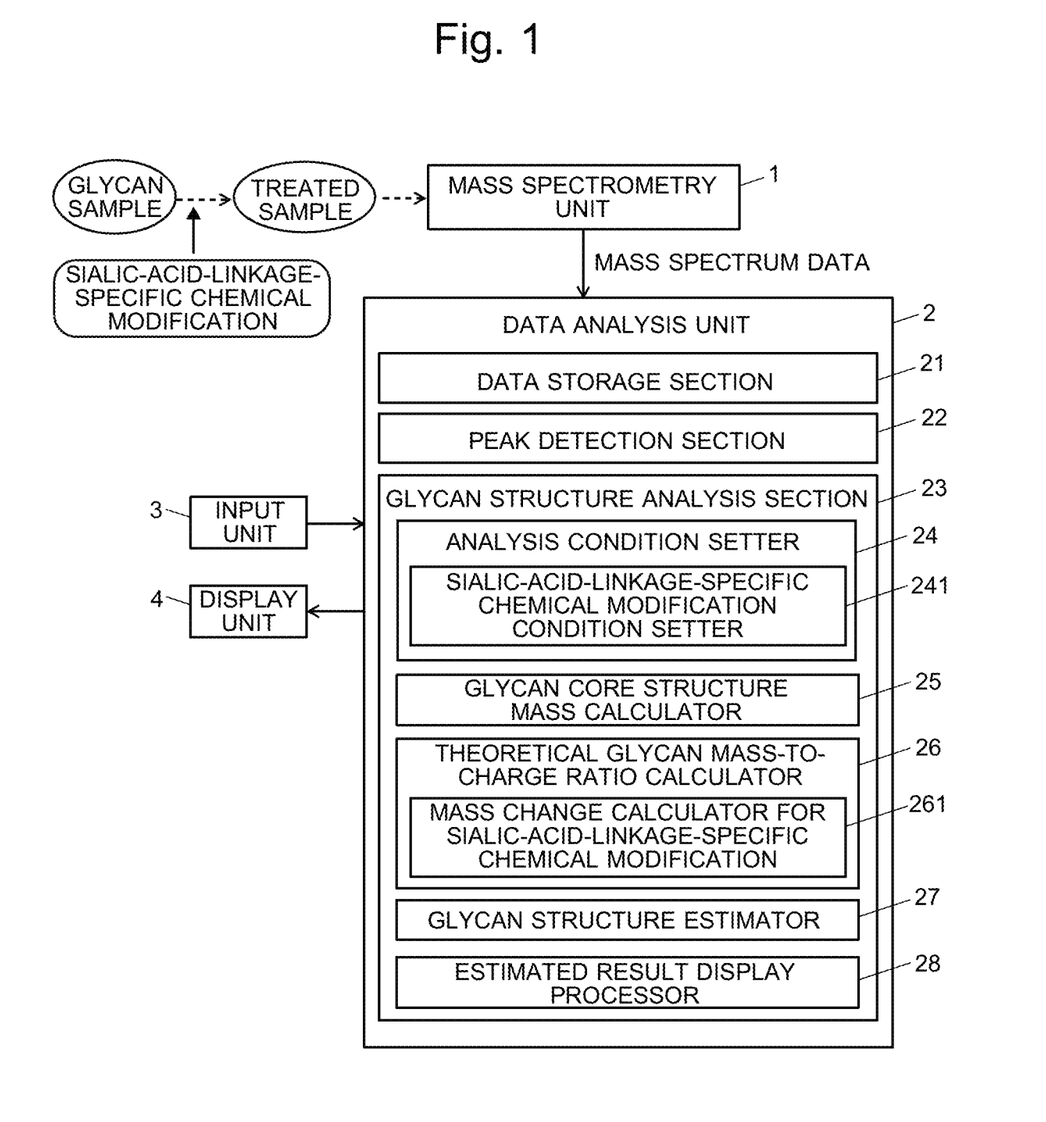
FIG. 1 is a schematic block configuration diagram of a glycan structure analyzing system as one embodiment of the present invention.

FIG. 1 is a schematic block configuration diagram of the glycan structure analyzing system according to the present embodiment. As shown in FIG. 1, the present system includes a mass spectrometry unit 1 which performs a measurement on a sample, a data analysis unit 2 which performs an analytical processing, as well as an input unit 3 and display unit 4 which are user interfaces. The data analysis unit 2 includes a data storage section 21, peak detection section 22 and glycan structure analysis section 23. The glycan structure analysis section 23 includes, as its functional blocks, an analysis condition setter 24, glycan core structure mass calculator 25, theoretical glycan mass-to-charge ratio calculator 26, glycan structure estimator 27 and estimated result display processor 28. Furthermore, the analysis condition setter 24 includes, as its sub-functional block, a sialic-acid-linkage-specific chemical modification condition setter 241, which is characteristic of the present embodiment. The theoretical glycan mass-to-charge ratio calculator 26 includes, as its sub-functional block, a mass change calculator for sialic-acid-linkage-specific chemical modification 261.

The type of the mass spectrometry unit 1 is not specifically limited. In general, it should have a high level of mass accuracy and mass-resolving power. Therefore, for example, a time-of-flight mass spectrometer (TOFMS) or Fourier-transform ion cyclotron resonance mass spectrometer (FT-ICRMS) is useful. As for the ionization method in the mass spectrometer, the matrix-assisted laser desorption/ionization (MALDI) can be used. Other methods are also available, such as the electrospray ionization (ESI) or probe electrospray ionization (PEST), although the MALDI is preferable in that this method mainly generates singly-charged ions.

As will be described later, a normal mode of mass spectrometry which includes no dissociation of ions is often sufficient for the glycan structure analysis including the numbers and linkage types of the sialic acids modifying the glycan. However, for the structural analysis of a peptide or similar molecule to which a glycan is linked, it is common to perform an $MS^n$ analysis with n being equal to or greater than two to acquire $MS^n$ spectrum data. In that case, a mass spectrometer including an ion trap, collision cell or similar function for dissociating an ion by a collision induced dissociation (CID) or similar process is used as the mass spectrometry unit 1.

The mass spectrometry unit 1 does not need to be an independent mass spectrometer. A liquid chromatograph mass spectrometer (LC-MS) may also be used. It may also be a system in which an eluate containing sample components separated from each other by a liquid chromatograph is preparatively fractionated to prepare a plurality of specimens, and those specimens are individually subjected to mass spectrometry in a mass spectrometer.

The data analysis unit 2 in the present system is actually a general-purpose personal computer or more sophisticated workstation, with the functions of the functional blocks shown in FIG. 1 realized by executing, on the computer, a dedicated data processing program installed on the same computer. This data processing program corresponds to the glycan structure analysis program according to the present invention. In that case, the input unit 3 includes a keyboard and pointing device (e.g., mouse) provided for the computer, while the display unit 4 includes the monitor provided for the same computer. The data processing program can be offered to users in the form of a non-transitory storage medium recording the program, such as a CD-ROM, DVD-ROM, memory card, or USB memory (dongle). It may also be offered to users in the form of data transferred through the Internet or similar communication networks.

When a glycan structure analysis is to be performed with the system according to the present embodiment, a sample containing a glycan ("glycan sample") should be pretreated by a sialic-acid-linkage-specific chemical modification, and the treated sample is subjected to mass spectrometry in the mass spectrometry unit 1 to acquire mass spectrum data covering a predetermined range of mass-to-charge ratios. As one example, it is hereinafter assumed that a sialic-acid-linkage-specific chemical modification as described in Patent Literature or Non Patent Literature 1 is performed in which the glycan sample is subjected to the reaction under the presence of a dehydration-condensation agent containing an amine and carbodiimide. In that case, if the sialic acid in the glycan is in an α2,3-linked type, a lactone is formed as the modifier. If the sialic acid in the glycan is in an α2,6-linked type, an amide is formed as the modifier. Although the glycans originally have the same composition, the modifiers differ from each other in mass. The mass spectrum data acquired in the mass spectrometry unit 1 for a sample which has been treated by the previously described chemical modification is sent to the data analysis unit 2 and stored in the data storage section 21.

In the data analysis unit 2, the peak detection section 22 detects peaks in the collected mass spectrum data according to a predetermined algorithm, and acquires the mass-to-charge ratio and signal intensity of each peak to create a peak list. The created peak list is temporarily stored in the data storage section 21. This peak list will be the data to be analyzed by the glycan structure analysis section 23.

Figure 3:
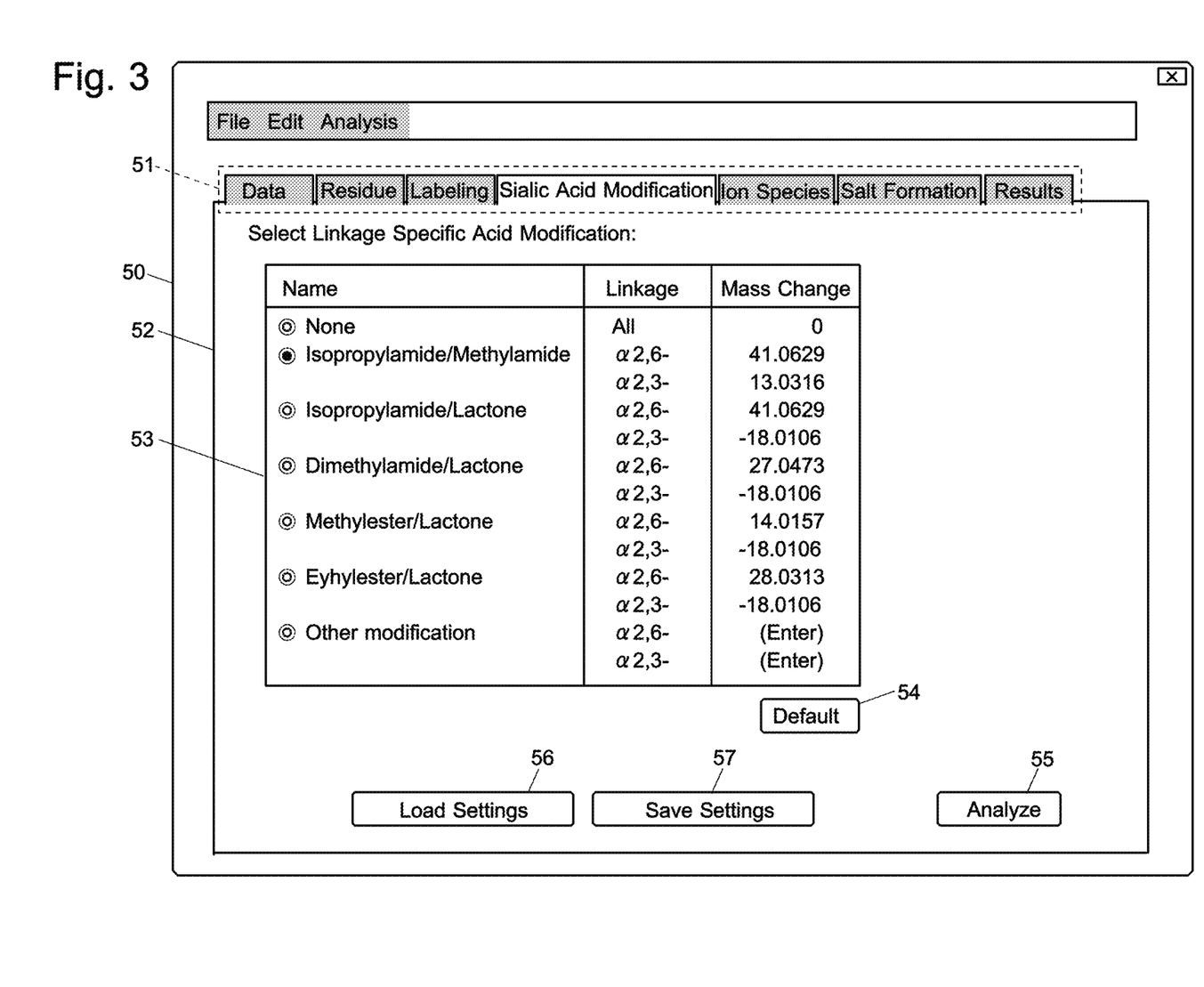
FIG. 3 shows one example of the tab which allows a user to set a sialic-acid-linkage-specific chemical modification in the glycan structure analyzing system according to the present embodiment.

To carry out a glycan structure analysis, the user initially performs a predetermined operation from the input unit 3. In response to this operation, the analysis condition setter 24 displays a main window on the screen of the display unit 4. The main window has a plurality of switchable tabs. FIG. 3 shows the main window 50 in which one of the tabs, named the "Sialic Acid Modification" setting tab 52, is opened. Other than this "Sialic Acid Modification" setting tab 52, the window is provided with the "Data" setting tab, "Residue" setting tab, "Labelling" setting tab, "Ion Species" setting tab, "Salt Formation" setting tab, and result display tab (labelled "Results" in FIG. 3). The user can easily switch between those tabs by clicking a desired tab in a tab switching area 51.

The result display tab is a tab for displaying the result of the glycan structure analysis. The other tabs are used for setting analysis conditions and other items of information before the execution of the analysis, or issuing a command to execute the analysis.

Schematic descriptions of those tabs are as follows:

The "Data" setting tab allows the user to select a peak list to be analyzed, and input numerical values, such as the allowable mass error of the measurement data. The inputted values determine the allowable error to be used when the mass-to-charge ratio of a measured ion peak is compared with theoretical glycan mass-to-charge ratios, as will be described later.

The "Residue" setting tab allows the user to set the kinds of sugars and other molecules to be considered in estimating the glycan composition, as well as the condition on the number of occurrences of each kind of sugar. For example, on the "Residue" setting tab allows the selection of the kind of sugar from monosaccharides, including sialic acids, such as hexose, N-acetyl hexosamine, deoxyhexose, N-acetyl neuraminic acid, N-glycolyl neuraminic acid, KDN (2-keto-3-deoxy-D-glycero-D-galacto-nononic acid) or pentose, as well as the setting of the condition on the number of occurrences of the selected kind of sugar. The selection and setting for other kinds of molecules, such as phosphorus or sulfur, can also be performed. If the number of occurrences is set to zero, it means that the glycan does not include the monosaccharide or molecule concerned.

The "Labelling" setting tab allows the user to select the kind of modification by the labelling, a primary example of which is the fluorescent labelling. For example, 2-amino benzamide, pyridylamine or other labelling substances can be selected on the "Labelling" setting tab.

The "Ion Species" setting tab allows the user to select the polarity, number of charges, and ion species of an ion produced by the ionization of the glycan. As for the ion species, the "Ion Species" setting tab allows the selection from the proton ($H^+$) addition, sodium ($Na^+$) addition, potassium ($K^+$) addition and other reactions for positive ions, as well as the proton ($H^-$) elimination, chlorine ion ($Cl^-$) addition, phosphoric ion ($H_2PO_4^-$) addition and other reactions for negative ions.

The "Salt Formation" setting tab allows the user to perform the setting of the substitution of a partial structure of the glycan that involves no change in the number of charges. The "Salt Formation" setting tab allows the selection of the substitution of sodium, potassium or lithium for proton. Furthermore, the upper limit of the number of substitutions can also be specified.

The "Sialic Acid Modification" setting tab 52, shown in FIG. 3, is displayed by the sialic-acid-linkage-specific chemical modification condition setter 241. This tab allows the user to select the kind of sialic-acid-linkage-specific chemical modification. As shown in FIG. 3, the "Sialic Acid Modification" setting tab 52 has a setting target area 53 with radio buttons which allow the selection of one of the seven options, including no modification ("None" in FIG. 3), five preset sialic-acid-linkage-specific chemical modifications, and undefined sialic-acid-linkage-specific chemical modification ("Other modification" in FIG. 3). For each of the five preset sialic-acid-linkage-specific chemical modifications, the amount of mass change ("Mass Change" in FIG. 3) based on a known change in chemical formula is defined for each of the two linkage types, i.e., α2,3 and α2,6 linkages. This allows the user to conveniently select preset values for chemical modifications which are rather frequently used, as with isopropyl amine.

In the case of using an undefined chemical modification agent which is not included in the preset chemical modifications, the user selects the "Other Modification" option and inputs a numerical value of the amount of mass change based on a change in chemical formula for each of the α2,3 and α2,6 linkages. This requires the user to perform only simple operations and proceed with the analysis even in the case of using a new or rather uncommon chemical modification agent which has not been assumed for use. It should be noted that clicking the "Default" button 54 on the "Sialic Acid Modification" setting tab 52 in FIG. 3 resets the information in the setting target area 53 to the default settings registered in a previously specified file.

When the "Save Settings" button 57 on the "Sialic Acid Modification" setting tab 52 is clicked by the user, the information which has been set in the setting target area 53 at that point in time is saved in a previously specified setting-information-saving file. On the other hand, when the "Load Settings" button 56 is clicked by the user, the information held in the setting-information-saving file is automatically set in the setting target area 53. With this function, for example, the user only needs to perform a simple operation to conduct an analysis under the same condition as an analysis performed in the past.

Figure 5:
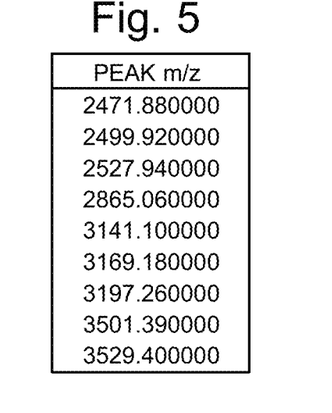
FIG. 5 shows an example of the mass-to-charge ratios of ion peaks to be analyzed.
Figure 6:
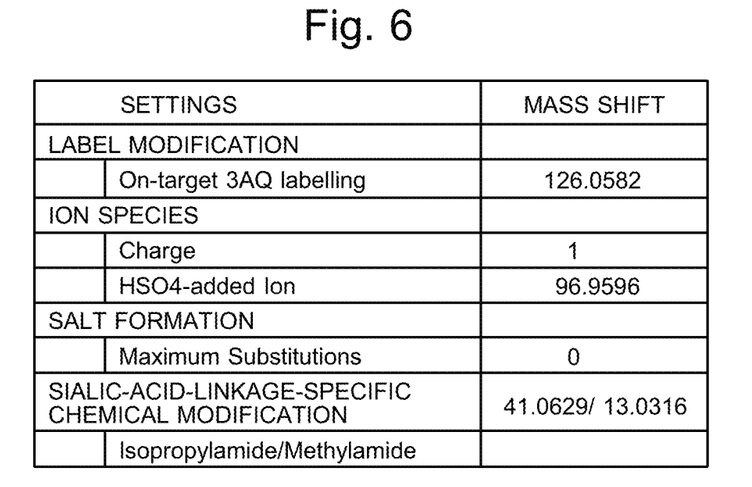
FIG. 6 shows one example of the search conditions set by a user.
Figure 7:
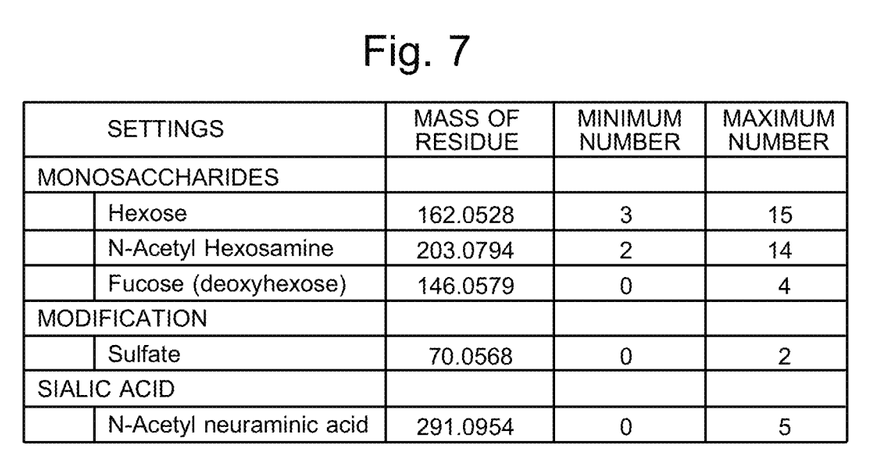
FIG. 7 shows one example of the limiting conditions for determining all possible core glycan structures.

The user performs appropriate settings concerning the analysis conditions on the tabs of the main window in the previously described manner (Step S1). FIG. 5 shows an example of the peak list set on the "Data" setting tab. FIG. 6 shows a setting example of the items of information in the case of using isopropyl amine as the sialic-acid-linkage-specific chemical modification agent. FIG. 7 shows an example of the glycan search condition set on the "Residue" setting tab. For example, the settings in FIG. 7 mean that the search must search all glycans in which the number of occurrences of hexose is between 3 and 15, inclusive. As for the sialic acid, the settings mean that the search must search all glycans in which the number of occurrences of N-acetyl neuraminic acid is between 0 and 5, inclusive.

When the "Analyze" button 55 is clicked on the "Sialic Acid Modification" setting tab 52 (or another setting tab) by the user, the glycan structure analysis section 23 responds to the operation and actually initiates the analytical processing under the set analysis conditions.

Figure 2:
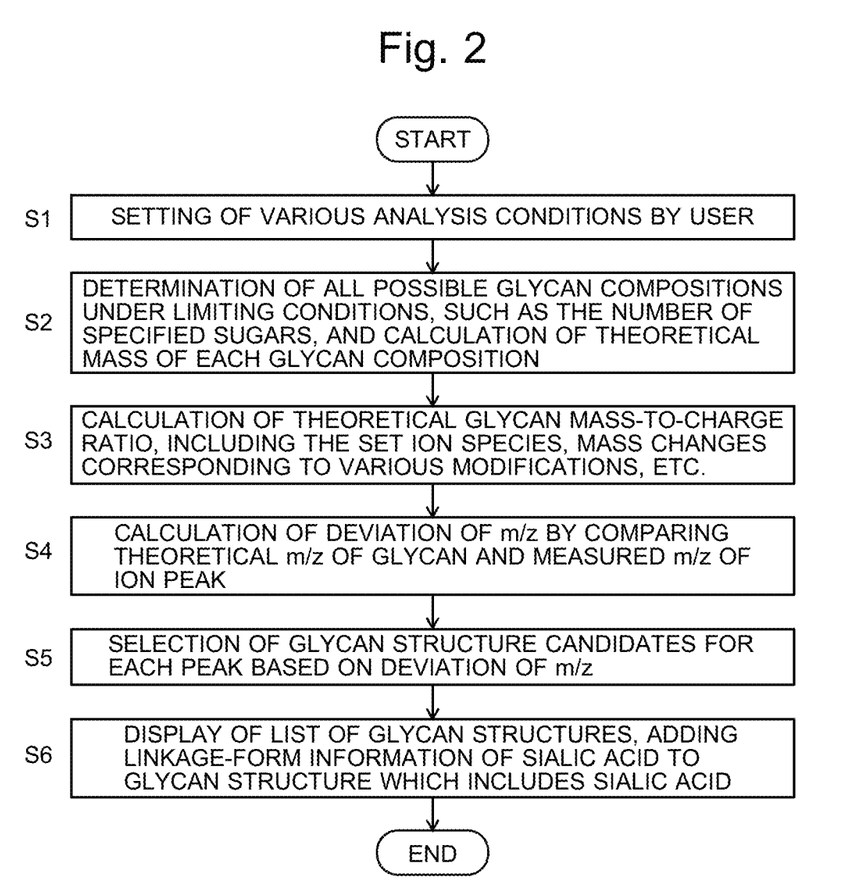
FIG. 2 is a flowchart of the procedure of the analyzing process in the glycan structure analyzing system according to the present embodiment.

That is to say, initially, the glycan core structure mass calculator 25 creates all possible combinations according to the glycan search conditions set on the "Residue" setting tab to determine all possible glycan compositions. Those glycan compositions do not reflect the glycan structure, such as the number of branches. For each of the possible glycan compositions, the glycan core structure mass calculator 25 calculates the theoretical mass of the glycan by adding the theoretical masses of monosaccharides and other molecules (Step S2). The obtained value is the theoretical mass of the glycan which has not undergone any modification or other reactions, and is not ionized yet.

For each of the glycans having different compositions, the theoretical glycan mass-to-charge ratio calculator 26 calculates a theoretical mass-to-charge ratio of the glycan after the ionization into the ion species, modification, substitution or other reactions which are set as the search conditions (Step S3). For example, consider the case where isopropyl amine is used as the sialic-acid-linkage-specific chemical modification agent as in the setting example shown in FIG. 6. In this case, the increase in mass due to the modification is 13.0316 for $\alpha 2,3$-linked sialic acid, or 41.0629 for $\alpha 2,6$-linked sialic acid. Accordingly, for a glycan including n $\alpha 2,3$-linked sialic acids, a mass-to-charge ratio of $13.0316 \times n$ is added to the mass-to-charge ratio of the glycan ion. On the other hand, for a glycan including n $\alpha 2,6$-linked sialic acids, a mass-to-charge ratio of $41.0629 \times n$ is added to the mass-to-charge ratio of the glycan ion. The same also applies to the labelling modification or substitution. Thus, from one glycan having a specific glycan composition, a plurality of theoretical mass-to-charge ratios are calculated according to the difference in modification or substitution. Therefore, if at least one sialic acid is included the glycan, the difference in linkage type of the sialic acid is reflected in the theoretical mass-to-charge ratio.

Subsequently, the glycan structure estimator 27 sequentially compares the mass-to-charge-ratio values (measured values) of the ion peaks in a given peak list with the theoretical mass-to-charge ratios (theoretical values) of each glycan calculated in Step S3. Specifically, for each ion peak, the deviation between the measured and theoretical values of the mass-to-charge ratio is calculated (Step S4), and each glycan having a deviation falling within a previously set allowable error is extracted as a glycan structure candidate corresponding to that ion peak (Step S5). In normal cases, there are a plurality of glycan structure candidates corresponding to one ion peak since the number of theoretically estimated glycans (modifiers) is enormous. In the case of a glycan including a sialic acid, the glycan structures which correspond to that glycan yet show different theoretical mass-to-charge ratios contain information concerning the linkage type of the sialic acid, i.e., information showing whether the sialic acid is in the $\alpha 2,3$-linked or $\alpha 2,6$-linked type.

One or more glycan structure candidates are extracted for each peak, and each glycan structure candidate has corresponding information of the deviation of the mass-to-charge ratio. Accordingly, for each ion peak, the estimated result display processor 28 creates a screen showing a list of the glycan structure candidates including the information of the linkage type of the sialic acid. When the result display tab is opened by the user, the estimated result display processor 28 displays the list of the glycan structure candidates on the tab (Step S6).

FIG. 4 shows a result of the estimation of the glycan structure for a glycan ion in the case where the sialic-acid-linkage-specific chemical modification was performed using isopropyl amine. This is the result of the estimation of the glycan structure under the conditions shown in FIGS. 5-7.

For example, in FIG. 4, the first glycan composition candidate corresponding to the ion peak at m/z 2471.88 incudes Neu5Ac($\alpha 2,3$), and therefore, is a glycan having one $\alpha 2,3$-linked sialic acid. The first glycan composition candidate corresponding to the ion peak at m/z 2499.92 incudes both Neu5Ac($\alpha 2,3$) and Neu5Ac($\alpha 2,6$), and therefore, is a glycan having one $\alpha 2,6$-linked sialic acid and one $\alpha 2,3$-linked sialic acid. Thus, if a sialic acid is included in the glycan composition, the information of its linkage type is displayed along with the composition. The user can obtain not only the number of sialic acids included in the glycan composition, but also the information of the linkage type of each sialic acid.

Thus, with the data analysis unit 2 in the glycan structure analyzing system according to the present embodiment, the user can obtain not only the number of sialic acids included in a glycan, but also the information of the linkage type of each sialic acid, by simply selecting, as one search condition, the chemical modification agent used for the pretreatment in order to determine the sialic-acid linkage type.

In the glycan structure analyzing system according to the previous embodiment, a glycan structure having a core structure is estimated by testing all possibilities under previously set restrictions concerning the kinds and numbers of sugars and other related molecules. It is also possible to determine the glycan structure having a core structure by using a previously created glycan structure database. In that case, various kinds of glycan structures and corresponding mass information are previously stored in the glycan structure database. The user sets a glycan mass range as a search condition instead of setting the conditions for estimating the glycan composition. The glycan core structure mass calculator 25 can perform a database search under the set mass condition and estimate glycan structure candidates which satisfy that condition.

It should be noted that the previous embodiment is a mere example of the present invention, and any change, modification, addition or the like appropriately made within the spirit of the present invention other than the previously described modified examples will also naturally fall within the scope of claims of the present application.

REFERENCE SIGNS LIST

1 . . . Mass Spectrometry Unit
2 . . . Data Analysis Unit
21 . . . Data Storage Section
22 . . . Peak Detection Section
23 . . . Glycan Structure Analysis Section
24 . . . Analysis Condition Setter
241 . . . Sialic-Acid-Linkage-Specific Chemical Modification Condition Setter
25 . . . Glycan Core Structure Mass Calculator
26 . . . Theoretical Glycan Mass-to-Charge Ratio Calculator
261 . . . Mass Change Calculator for Sialic-Acid-Linkage-Specific Chemical Modification
27 . . . Glycan Structure Estimator
28 . . . Estimated Result Display Processor
3 . . . Input Unit
4 . . . Display Unit
50 . . . Main Window
51 . . . Tab Switching Area
52 . . . "Sialic Acid Modification" Setting Tab
53 . . . Setting Target Area
54 . . . "Default" Button
55 . . . "Analyze" Button
56 . . . "Load Settings" Button
57 . . . "Save Settings" Button

The invention claimed is:

1. A glycan structure analyzer configured to determine a structure of a sialic-acid-linked glycan based on mass spectrum data obtained by a mass spectrometric analysis of a sample containing the sialic-acid-linked glycan pretreated with a chemical modification agent specific to the sialic-acid linkage type or a molecule modified with the glycan, the glycan structure analyzer comprising:
at least one processor configured to
allow a user to set an ion species to be analyzed, a polarity of an electric charge of the ion species, and mass change factors each of which causes a mass change of a glycan through a modification;
acquire various glycans having a core structure formed by a plurality of monosaccharide residues of a plurality of kinds, and mass information corresponding to each of those glycans;
calculate a theoretical glycan mass-to-charge ratio for each of the acquired various glycans by increasing or decreasing a mass of the glycan based on the mass change factors set by the user; and
estimate a structure of a glycan by comparing the theoretical glycan mass-to-charge ratio of the glycan with a mass-to-charge ratio of an ion peak in given mass spectrum data,
wherein:
the at least one processor is configured to allow the user to set, as one of the mass change factors, a chemical modification specific to a linkage type of a sialic acid separately from other kinds of modifications; and
the theoretical glycan mass-to-charge ratio is calculated for each sialic-acid linkage type according to the set chemical modification for sialic-acid-linkage-specific chemical modification.

2. The glycan structure analyzer according to claim 1, wherein:
when acquiring the various glycans having the core structure formed by the plurality of monosaccharide residues, the at least one processor is configured to estimate all possible glycan structures under specific limiting conditions concerning kinds and numbers of monosaccharide residues, and to determine various glycans having a core structure and mass information corresponding to each of those glycans.

3. The glycan structure analyzer according to claim 1, further comprising a glycan structure database recording various glycan structures and masses;
wherein the at least one processor is configured to determine various glycans having a core structure, by searching the information recorded in the glycan structure database, based on the mass information of the glycan set by the user.

4. The glycan structure analyzer according to claim 1, wherein:
the at least one processor is configured to output information concerning the estimated structure of the glycan, and is configured to output additional information showing the linkage type of each sialic acid if the estimated glycan structure includes sialic acids whose linkage types are identifiable.

5. The glycan structure analyzer according to claim 1, wherein:
the at least one processor is configured to allow a selection of a preset sialic-acid-linkage-specific chemical modification, as well as an input of a mass change value for each sialic-acid linkage type for other sialic-acid-linkage-specific chemical modifications.

6. A computer-readable non-transitory storage medium recording a glycan structure analysis program for determining a structure of a sialic-acid-linked glycan, using a computer, based on mass spectrum data obtained by a mass spectrometric analysis of a sample containing the sialic-acid-linked glycan pretreated with a chemical modification agent specific to the sialic-acid linkage type or a molecule modified with the glycan, wherein the program is configured:
to allow a user to set an ion species to be analyzed, the polarity of the electric charge of the ion species, and mass change factors each of which causes a mass change of a glycan through a modification;
to acquire various glycans having a core structure formed by a plurality of monosaccharide residues of a plurality of kinds, and mass information corresponding to each of those glycans;
to calculate a theoretical glycan mass-to-charge ratio for each of the acquired various glycans by increasing or decreasing the mass of the glycan based on the mass change factors set by the user; and
to estimate the structure of a glycan by comparing the theoretical glycan mass-to-charge ratio of the glycan with the mass-to-charge ratio of an ion peak in given mass spectrum data,
where:
the program is configured to allow the user to set, as one of the mass change factors, a chemical modification specific to a linkage type of a sialic acid, separately from other kinds of modifications; and the theoretical glycan mass-to-charge ratio is calculated for each sialic-acid linkage type according to the set chemical modification specific to the linkage type of the sialic acid.

7. The computer-readable non-transitory storage medium recording the glycan structure analysis program according to claim 6, wherein:

when acquiring the various glycans having a core structure formed by the plurality of monosaccharaide residues, the program is configured to estimate all possible glycan structures under specific limiting conditions concerning kinds and numbers of monosaccharide residues, and to determine various glycans having a core structure and mass information corresponding to each of those glycans.

8. The computer-readable non-transitory storage medium recording the glycan structure analysis program according to claim 6, wherein:

when acquiring the various glycans having a core structure formed by the plurality of monosaccharaide residues, the program is configured to determine various glycans having a core structure, by searching the information recorded in a glycan structure database recording various glycan structures and masses, based on the mass information of the glycan set by the user.

9. The computer-readable non-transitory storage medium recording the glycan structure analysis program according to claim 6, wherein:

the program is configured to output information concerning the estimated structure of the glycan, and is configured to output additional information showing the linkage type of each sialic acid if the estimated glycan structure includes sialic acids whose linkage types are identifiable.

10. The computer-readable non-transitory storage medium recording the glycan structure analysis program according to claim 6, wherein:

the program is configured to allow a selection of a preset sialic-acid-linkage-specific chemical modification, as well as an input of a mass change value for each sialic-acid linkage type for other sialic-acid-linkage-specific chemical modifications.

11. A method of determining a structure of a sialic-acid-linked glycan based on mass spectrum data obtained by a mass spectrometric analysis of a sample containing the sialic-acid-linked glycan pretreated with a chemical modification agent specific to the sialic-acid linkage type or a molecule modified with the glycan, implemented on at least one processor, comprising:

inputting conditions including an ion species to be analyzed, a polarity of an electric charge of the ion species, and mass change factors each of which causes a mass change of a glycan through a modification;

acquiring various glycans having a core structure formed by a plurality of monosaccharide residues of a plurality of kinds, and mass information corresponding to each of those glycans;

calculating a theoretical glycan mass-to-charge ratio for each of the acquired various glycans by increasing or decreasing a mass of the glycan based on the mass change factors input in the conditions; and estimating a structure of a glycan by comparing the theoretical glycan mass-to-charge ratio of the glycan with a mass-to-charge ratio of an ion peak in given mass spectrum data, wherein the initial conditions further include a mass change setting, as one of the mass change factors, configured to allow a user to input a chemical modification specific to a linkage type of a sialic acid separately from other kinds of modifications; and the theoretical glycan mass-to-charge ratio is calculated for each sialic-acid linkage type according to the set chemical modification for sialic-acid-linkage-specific chemical modification input.

* * * * *